United States Patent [19]

Glassman et al.

[11] Patent Number: 5,258,300
[45] Date of Patent: Nov. 2, 1993

[54] METHOD OF INDUCING LYSINE OVERPRODUCTION IN PLANTS

[75] Inventors: Kimberly F. Glassman, Minneapolis, Minn.; Linda J. Barnes, Ames, Iowa; William P. Pilacinski, Maple Grove, Minn.

[73] Assignee: Molecular Genetics Research and Development Limited Partnership, Minneapolis, Minn.

[21] Appl. No.: 204,388

[22] Filed: Jun. 9, 1988

[51] Int. Cl.$^5$ .................. A01H 4/00; C12N 15/32; C12N 5/14
[52] U.S. Cl. .................. 435/240.4; 800/205; 435/172.3; 536/237; 935/67
[58] Field of Search .................. 47/58; 800/1, 205; 435/68, 172.3, 317.1, 849, , 69.1, 320.1, 240.4; 935/67, 48; 536/27, 23.7

[56] References Cited

U.S. PATENT DOCUMENTS

| | | | |
|---|---|---|---|
| 4,346,170 | 8/1982 | Sano et al. | 435/172.3 |
| 4,535,060 | 8/1985 | Comai | 435/172.3 |
| 4,560,654 | 12/1985 | Miwa et al. | 435/172.3 |
| 4,642,411 | 2/1987 | Hibberd et al. | 800/200 |
| 4,769,061 | 9/1988 | Comai | 800/1 |

FOREIGN PATENT DOCUMENTS

| | | |
|---|---|---|
| 0189707 | 6/1986 | European Pat. Off. . |
| 0218571 | 4/1987 | European Pat. Off. ......... 435/172.3 |
| 0271408 | 6/1988 | European Pat. Off. . |
| 0240792 | 10/1987 | Fed. Rep. of Germany . |
| WO8704181 | 7/1987 | PCT Int'l Appl. . |

OTHER PUBLICATIONS

Dauce-LeReverend, et al. (1982) European J. Appl. Microbiol. Biotechnol. 15:227–231.
Richaud et al (1986) Journal of Bacteriology 166:297–300.
Shan et al (Jul. 1986) Science 233:478–481.
Vasil (Apr. 1988) Bio/Technology 6:397–402.
Yugari et al., Biochem. Biophys. Acta, 62, 612 (1962).

Primary Examiner—Che S. Chereskin
Attorney, Agent, or Firm—Merchant, Gould, Smith, Edell, Welter & Schmidt

[57] ABSTRACT

A method is provided for increasing the level of free L-lysine in a plant comprising: (a) introducing a foreign gene into the cells of a plant tissue source; and (b) expressing said foreign gene in said cells, wherein a first DNA sequence of said gene encodes dihydrodipicolinic acid synthase (DHDPS) which is substantially resistant to feedback inhibition by endogenously-produced free L-lysine.

16 Claims, 3 Drawing Sheets

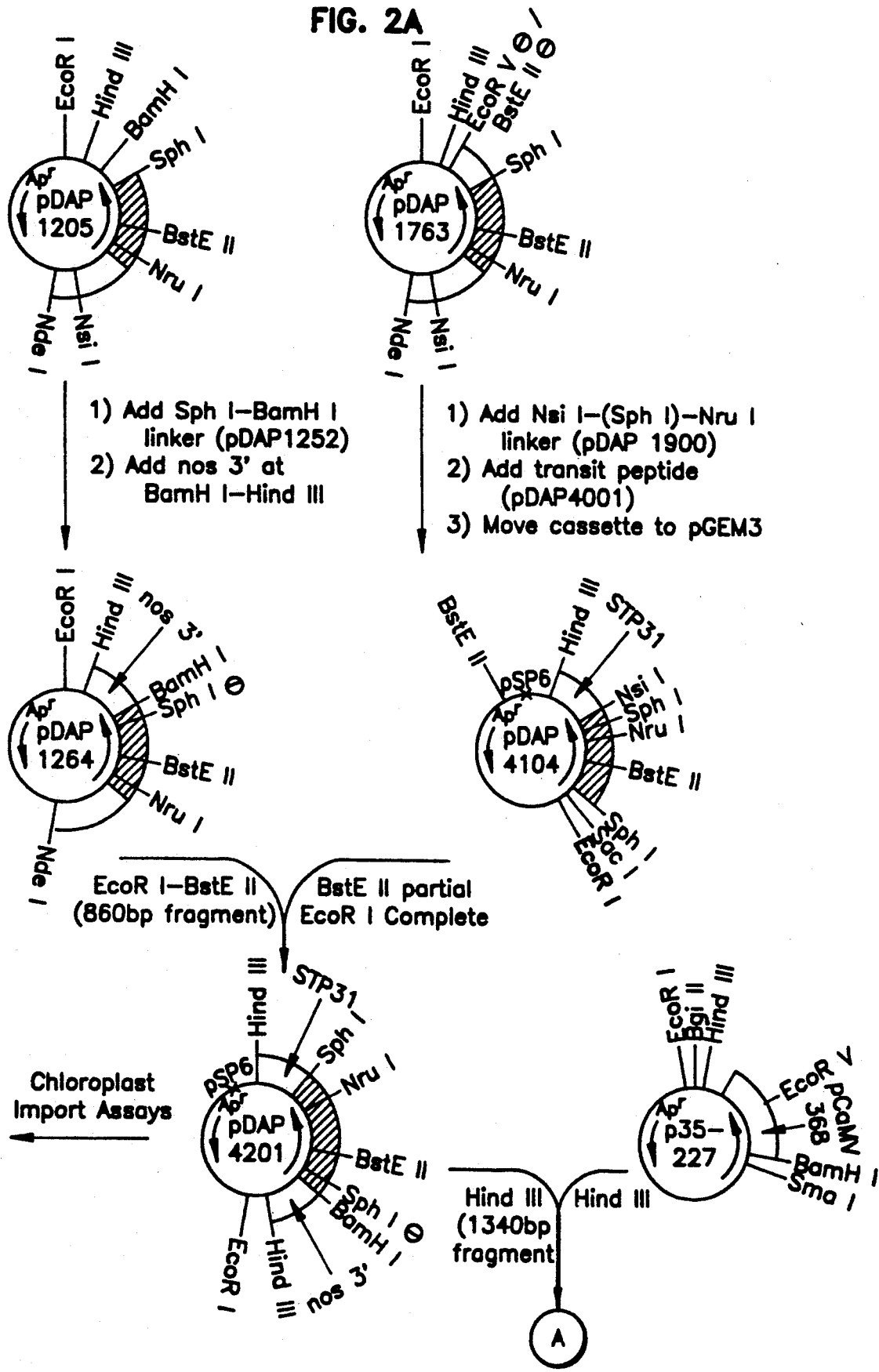

METHOD OF INDUCING LYSINE OVERPRODUCTION IN PLANTS

BACKGROUND OF THE INVENTION

Recent advances in gene transfer technology have opened up new possibilities for introducing desirable traits into plants. A number of such genes have been introduced, in order to confer upon the host plant some measure of protection against environmental stresses. Examples include genes conferring tolerance to chemical herbicides such as glyphosate (Comai, Nature, 317, 741-744 (1985) and Shah, Science, 233, 478-481 (1986)), phosphinothricin (De Block, EMBO, 6, 2513-2518 (1987)), bromoxynil (Stalker, 1987, International Patent Application No. PCT/US87/00044), and sulfonylureas (Haughn, Mol. Gen. Genet., 211, 266-271 (1988)). Transgenic plants have also been engineered to resist certain insect pests (Adang, 1985, published European Patent Application No. 142,924 and Vaeck, Nature, 328, 33-37 (1987)), fungal diseases (Taylor, Mol. Gen. Genet., 210, 572-577 (1987)), and viral diseases (Abel, Science, 232, 738-743 (1986) and Nelson, Bio/Technol., 6, 403-405 (1988)).

Another area of interest is the design of plants, especially crop plants, with added value traits. An example of such a trait is improved nutritional quality in food crops. Lysine, an amino acid essential in the diet of humans and monogastric animals, is among the three most limiting nutrients in most of the cereal crops. Consequently, grain-based diets, such as those based on corn, barley, wheat, rice, maize, millet, sorghum, and the like, must be supplemented with more expensive synthetic lysine or with lysine-containing oilseed protein meals. Increasing the lysine content of these grains or of any of the feed component crops would result in significant added value. To date, attempts to elevate lysine levels in plants have relied on conventional breeding methods and, more recently, mutagenesis and cell culture technology.

Naturally-occurring high lysine mutants of maize (Mertz, Science, 145, 279 (1964) and Nelson, Science, 150, 1469-1470 (1965)), barley (Munck, Science, 168, 985-987 (1970)), and grain sorghum (Singh et al., Crop Sci., 13, 535-539 (1973)) have been identified. In each case, the improved lysine content results not from increased free lysine production, but from shifts in the overall protein profile of the grain: the reduced levels of lysine-deficient endosperm proteins (prolamines) are complemented by elevated levels of more lysine-rich proteins (albumins, globulins and glutelins). While nutritionally superior, these mutants are associated with reduced yields and poor grain quality, limiting their agronomic usefulness.

An alternative approach used to improve nutritional quality has been in vitro selection for biochemical variants having elevated free lysine pools. Lysine is a member of the "aspartate family" of amino acids in higher plants and microorganisms (see FIG. 1). As such, the regulation of its biosynthesis is intimately connected to that of the other members of the family: threonine, methionine and isoleucine. Regulation of metabolite flow appears to be chiefly through endproduct feedback inhibition at key enzymatic steps. The first of these steps, the phosphorylation of aspartate catalyzed by aspartate kinase (AK), is common to all four endproducts. A second site of regulation is at the branch-point reaction: the condensation of pyruvate with aspartyl semialdehyde to form dihydrodipicolinic acid. This reaction is the first one unique to the biosynthesis of lysine and is catalyzed by dihydrodipicolinic acid synthase (DHDPS), an enzyme shown to be strongly feedback inhibited by lysine in plants where it has been examined (Wallsgrove et al., Phytochem., 20, 2651-2655 (1981), and Kumpaisal, Plant Physiol., 85, 145-151 (1987)).

There is evidence to suggest the existence of more than one form of AK (Miflin, 1980, in The Biochemistry of Plants, vol. 5, Amino Acids and Derivatives, Stumpf and Conn (eds.) pp 420-426, Academic Press). One form is sensitive to inhibition by threonine, the other to inhibition by lysine. The growth of plant cell cultures is inhibited in the presence of equimolar amounts of lysine plus threonine. This inhibition may be reversed by the addition of methionine or homoserine (which may be readily converted to methionine) (Green et al., Crop Sci., 14, 827-830 (1974)). Hibberd Planta, 148, 183-187 (1980)) selected stable lines of maize callus that were resistant to this growth inhibition. These lines overproduced threonine (6-9 fold) and to a lesser extent, methionine, lysine and isoleucine (2-4 fold). There was evidence that a lysine-tolerant AK was responsible for the changes observed. In the lines that were regenerated to whole, fertile plants, the overproduction was a stable, heritable trait (Hibberd et al., PNAS, 79, 559-563 (1982)). Similar selections have been carried out in tobacco (Bourgin, 1982, in Variability in Plants Regenerated from Tissue Culture, Earle and Demarly (eds.), pp 163-174, Praeger, New York), barley (Arruda, Plant Physiol., 76, 442-446 (1984)), and carrot (Cattoir-Reynaerts, Biochem Physiol. Pfanzen, 178, 81-90 (1983)).

Lysine analogs, in particular S(2-aminoethyl)cysteine (AEC) have also been used either alone or in conjunction with lysine plus threonine selections in attempts to isolate lysine-overproducing mutants. Sano et al. (J. Gen. Appl. Microbiol., 16, 373-391 (1970)) were able to isolate high lysine bacterial mutants using AEC selection and AEC was proposed to act as a false feedback inhibitor of AK or DHDPS or both. Attempts to isolate similar mutants in plants have had mixed results. Widholm (Can. J. Bot., 54, 1523-1529 (1976) mutagenized tobacco suspension cells and selected AEC-resistant cell lines that overproduced lysine by ten-fold. Pearl millet mutants were isolated that overproduced lysine by 5-7 fold (Boyes et al., Plant Sci., 50, 195-203 (1987)). Bright (Planta, 146, 629-633 (1979)) selected AEC-resistant barley lines that did not accumulate lysine in the absence of AEC and were shown to be AEC uptake mutants. There was also evidence that AEC exerted its inhibitory effects by being incorporated into proteins rather than by interfering with lysine biosynthesis. Schaeffer et al. (Plant Physiol., 84, 509-515 (1987)) applied sequential AEC and lysine plus threonine selections to obtain race mutants that had 14% higher lysine in seed storage proteins, but not higher free lysine. An AEC-resistant potato culture was selected by Jacobsen (J. Plant Physiol., 123, 307-315 (1986)). This mutant had higher overall amino acid levels than control cultures but this was not due to overproduction of lysine, threonine or methionine. Negrutiu (Theor. Appl. Genet., 68, 11-20 (1984)) subjected tobacco protoplasts to mutagenesis followed by AEC selection. Two resistant cell lines were obtained that overproduced lysine by 10-30 fold. Biochemical and genetic analysis revealed a feedback-insensitive DHDP synthase. The trait was inherited as a single dominant gene.

Heretofore, recombinant DNA and gene transfer technologies have not been applied to the area of increased metabolite production for added value in plants. However, it is known that the bacterium *Escherichia coli* synthesizes lysine by a pathway essentially identical to that of higher plants. Dihydrodipicolinic acid synthase is encoded by the dap A gene of *E. coli* and, while sensitive to lysine (Yugari et al., *Biochim. Biophys. Acta*, 62, 612–614 (1962)), it is at least 200-fold less sensitive to inhibition by lysine in vitro when compared to the same enzyme isolated from plants. Further, *E. coli* cells carrying the dap A gene on a multicopy plasmid accumulate high levels of free lysine (Dauce-LeReverand, *Eur. J. Appl. Microbiol. Biotechnol.*, 15, 227–231 (1982)), suggesting that DHDPS catalyzes a rate-limiting step. The gene has been sequenced and characterized (Richaud, *J. Bacteriol.*, 166, 297–300 (1986)) and Glassman, 1988, M.S. Thesis, University of Minnesota, Minneapolis, MN).

Considering the relative inability of conventional breeding and tissue culture technology to readily obtain plants accumulating significantly higher levels of lysine, a need exists to apply recombinant DNA and gene transfer technology to produce such plants.

SUMMARY OF THE INVENTION

The present invention provides a method of substantially increasing the level of free L-lysine in a plant comprising: (a) introducing a foreign gene into the cells of a plant tissue source, and (b) expressing the foreign gene in said cells, wherein said foreign gene comprises a DNA sequence which encodes dihydrodipicolinic acid synthase (DHDPS) which is substantially resistant to feedback inhibition by endogenously-produced free L-lysine. In the practice of the present method, the foreign gene comprises a second DNA sequence which is attached to the 5'-terminus of the DHDPS DNA sequence, and which encodes a chloroplast transit peptide (CTP). The CTP localizes the DHDPS in the chloroplasts of said cells, where it can act to enhance the biosynthesis of free L-lysine.

Therefore, the present method also provides plant cells which have been transformed by the introduction of a foreign gene which expresses a form of DHDPS which is substantially-resistant to feedback inhibition by endogenous lysine. Since techniques are known by which cells from a wide variety of plant tissue sources can be regenerated into whole plants, the present method also provides a transformed plant which produces free L-lysine by a biosynthetic pathway employing DHDPS, wherein the DHDPS is the product of a foreign (exogenous) gene, and is substantially resistant to feedback-inhibition by endogeneously-produced lysine. Preferred plants which are transformed by the present method include the graminaceous species, such as those enumerated hereinabove. The edible parts of such transformed plants can have free L-lysine levels which are at least about 50 times higher than the lysine levels in an untransformed plant of the same species.

The foreign gene employed to transform the plant cells is preferably a chimeric-gene expression cassette comprising a gene coding for DHDPS or an enzymatically-functional fragment thereof which is substantially resistant to feedback inhibition. The expression cassette also comprises a second DNA sequence which encodes an amino-terminal chloroplast transit sequence (CTS). The DHDPS gene or gene fragment is joined in correct reading frame at its 5'-terminus to the CTS gene. The foreign gene is preferably under the transcriptional and translational control of regulatory regions which are functional in the target plant cells. Such regions can be obtained from the DNA sequences which are transferred to plant cells by the Ti or Ri plasmids of *A. tumefaciens*, e.g., segments of the "T DNA." For example, a useful transcriptional initiation region can be isolated from a Ti or Ri plasmid gene encoding octopine synthase, nopaline synthase or mannopine synthase. The expression cassette preferably further comprises a gene encoding a function that is selectable in plant cells, such as drug or herbicide resistance, so that the transformed cells, and the plants derived therefrom, can be readily identified.

A further embodiment of the present invention comprises an expression vector such as a plasmid, which incorporates the present expression cassette, wherein said plasmid is capable of replication in a bacterium such as *E. coli* or Agrobacterium. The foreign gene can be introduced into the genome of the plant cells as "naked" DNA by methods such as electroporation, microinjection, microprojectile injection or via liposome encapsulation. Also, a plasmid incorporating the foreign gene can be introduced into the genome of the plant cells by *A. tumefaciens*-mediated transformation.

As used herein with respect to a gene or gene fragment, the term "foreign" means that the gene or gene fragment is obtained from one or more sources other than the genome of the species of plant within which it is ultimately expressed. The source can be natural, e.g., the gene can be obtained from another source of living matter, such as bacteria, yeast, fungi and the like, or a different species of plant. A preferred source of a gene encoding functional DHDPS is the *E. coli dap* A gene. The source can also be synthetic, e.g., the gene or gene fragment can be prepared in vitro by chemical synthesis.

As used herein with respect to a foreign gene or gene fragment which has been introduced into plant cells, the term "expresses" means that the gene is stably incorporated into the genome of the cells, so that the product encoded by the gene, e.g., an enzyme such as DHDPS, is produced in a functional form within the cells. For example, a functional form of DHDPS catalyzes a step in the endogenous biosynthesis of lysine.

As used herein with respect to the feedback inhibition of DHDPS by endogenous lysine, the term "substantially resistant" means that the DHDPS remains functional in the presence of endogenous lysine to the extent that the plant accumulates lysine substantially in excess of that accumulated by a plant of the same species which does not synthesize DHDPS which is so resistant. For example, novel plants resulting from the present method contain extractable lysine levels at least about ten times, and preferably, at least about 50 times, e.g., about 50–250 times higher than plants of the same species which contain only native DHDPS. Furthermore, free lysine is not present in levels which are toxic to the particular plant species which has been altered. Also, plant cells or plants which are referred to as "transformed" have the foreign gene or gene fragment stably, functionally and inheritably integrated into their genome.

DETAILED DESCRIPTION OF THE INVENTION

Figure 1:
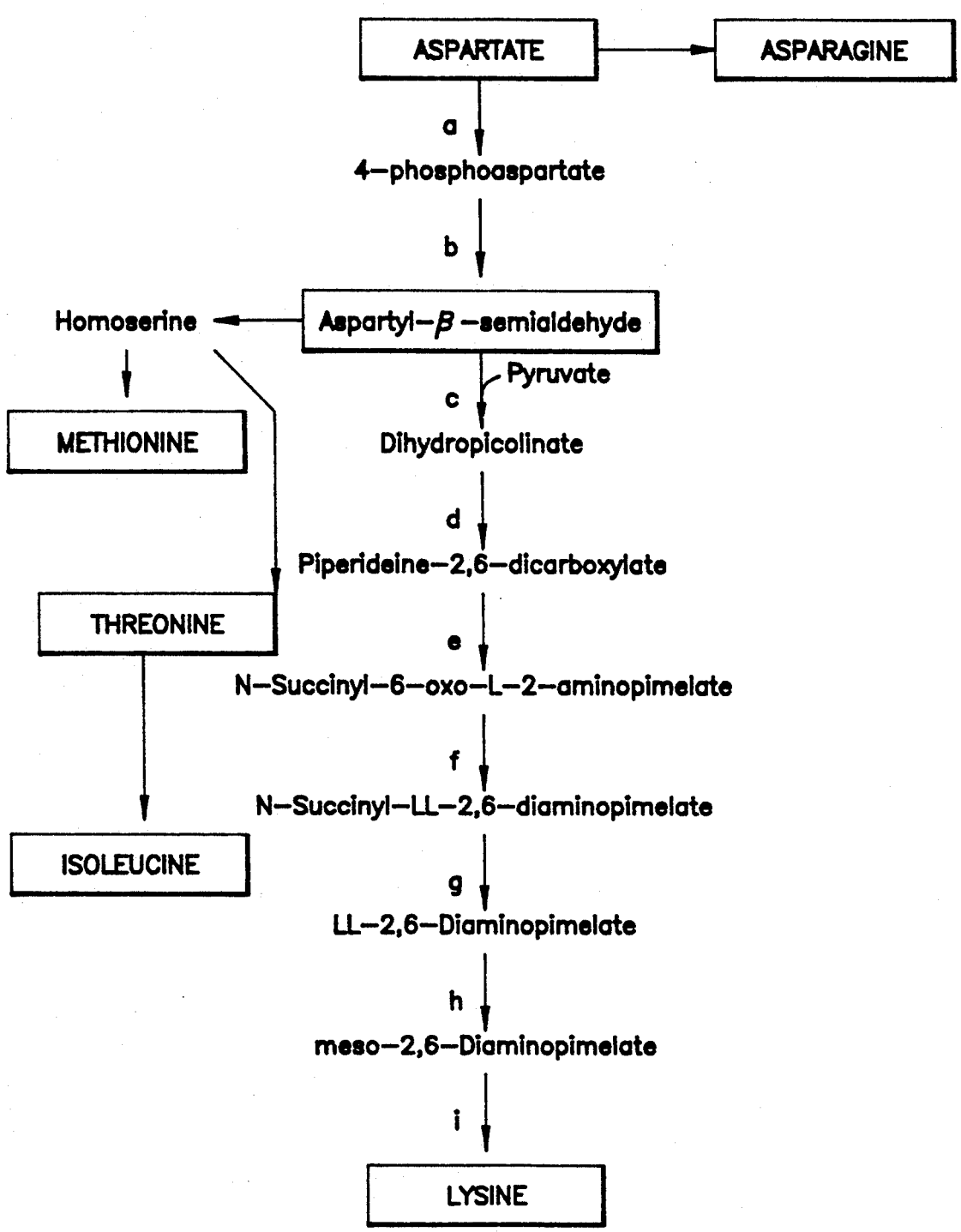
FIG. 1 is a schematic depiction of the lysine biosynthetic pathway wherein the following letters indicate the following enzymes: a—aspartate kinase; b—aspartyl-semialdehyde dehydrogenase; c—dihydrodipicolinic acid synthase; d—dihydrodipicolinic acid reductase; e—succinyloxoaminopimelate synthase; f—succinyldiaminopimelate amino transferase; g—succinyldiaminopimelate desuccinylase; h—diaminopimelate; and i—meso-diaminopimelate decarboxylase.
Figure 2B:
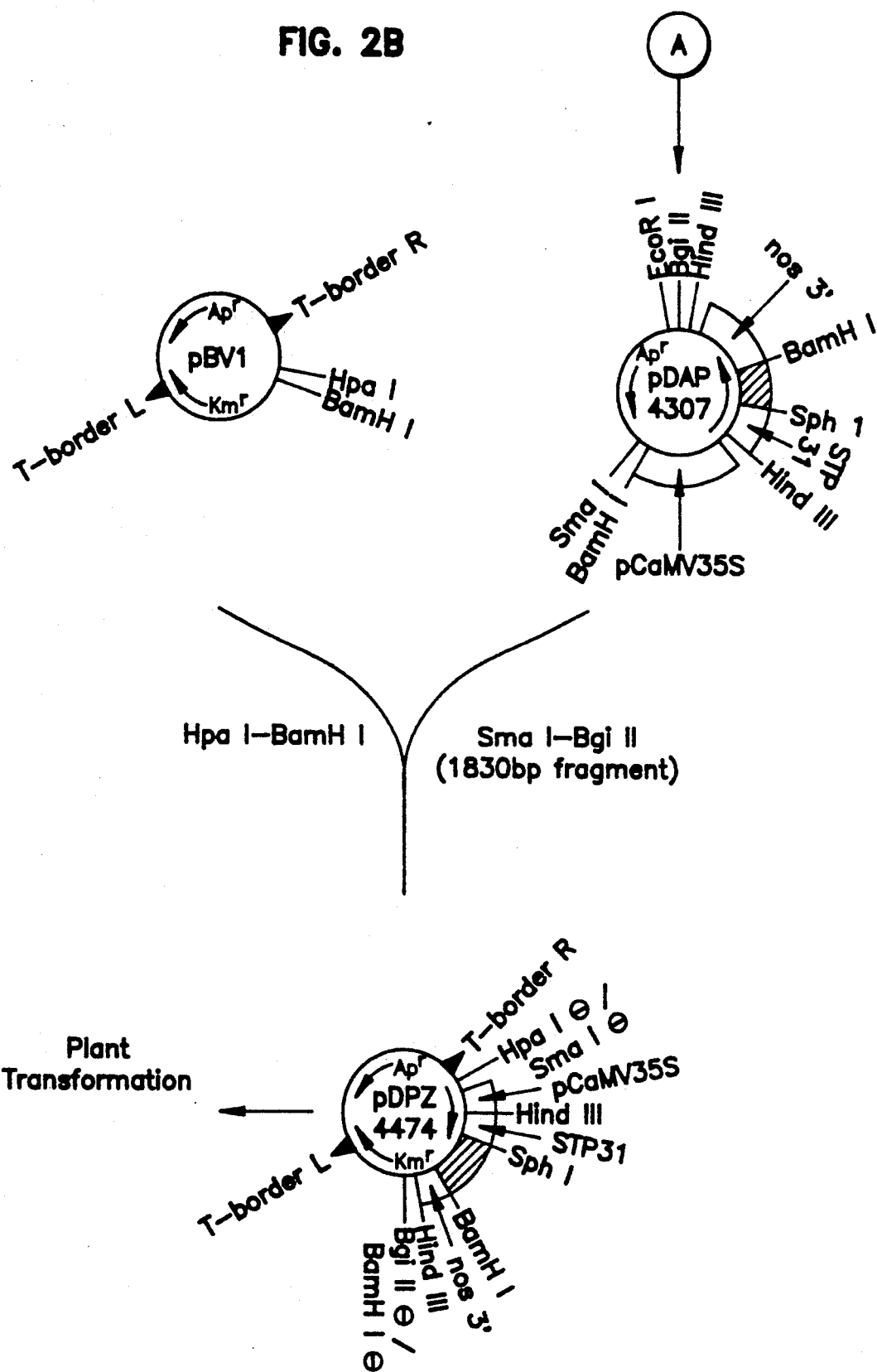
FIG. 2 schematically depicts the manipulation of the dap A gene as described in Example I.

The present invention relates to a novel method for obtaining plants, such as the grains, that produce elevated levels of free lysine. The overproduction results from the introduction and expression of an introduced bacterial gene encoding dihydrodipicolinic acid (DHDP) synthase, the branch-point enzyme in the biosynthesis of lysine in both plants and bacteria. Native plant DHDP synthase is highly sensitive to feedback inhibition by L-lysine and constitutes a key site of regulation of the pathway. By contrast, DHDP synthase isolated from *Escherichia coli* is active in the presence of at least 200-fold higher levels of L-lysine.

In order for the introduction of a gene encoding a lysine-tolerant DHDP synthase to result in the accumulation of higher levels of free lysine in a plant, a long and complex chain of events must occur.

In the first place, the bacterial DHDP synthase gene must be modified in vitro to include regulatory signals required for gene expression in plant cells. Because the lysine biosynthetic pathway in plants is reported to be sequestered in the chloroplasts, the bacterial gene is preferably modified to add sequences encoding an amino-terminal chloroplast transit peptide sequence, in order to direct the gene product to these organelles.

In order to alter the biosynthesis of lysine, the gene must be introduced into the plant cells and these transformed cells identified. The gene must also be stably incorporated into the plant cell genome. The transcriptional signals of the gene must be recognized by and be functional in the plant cells. That is, the gene must be transcribed into messenger RNA, and the mRNA must be stable in the plant nucleus and be transported intact to the cytoplasm for translation. The gene must have appropriate translational signals to be recognized and properly translated by plant cell ribosomes. The polypeptide gene product must escape proteolytic attack in the cytoplasm and be able to assume a three-dimensional conformation that will confer enzymic activity. The bacterial DHDP synthase must further be able to function in the biosynthesis of lysine; that is, it must be localized near the native plant enzymes catalyzing the flanking steps in biosynthesis (presumably in the chloroplast) in order to obtain the required substrates (aspartyl semialdchyde and pyruvate) and to pass on the appropriate product (dihydropicolinic acid).

Even if all these conditions are met, successful overproduction of lysine is not a predictable event. There must be no other control mechanism compensating for the reduced regulation at the DHDP synthase step. This means not only no other inhibition of biosynthesis, but also no mechanism to increase the rate of breakdown of the accumulated lysine. Lysine must be also overproduced at levels which are not toxic to the plant. Finally, the introduced trait must be stable and heritable in order to permit commercial development and use.

Modification of a Bacterial Gene for Expression and Function in Plant Cells

A gene encoding dihydrodipicolinic acid synthase (DHDPS) can be obtained from any microorganism that synthesizes lysine by the diaminopimelate pathway. A key criterion in the choice of gene is the relative insensitivity of the gene product (DHDPS) to inhibition by lysine. One such gene, which is a preferred starting material for use in the present method, is the *E. coli* dap A gene, which encodes a functional 32 kD species of DHDPS which is highly resistant to feedback inhibition by lysine. The gene may be isolated from the microorganism by methodologies well known in the art. Such methodologies include screening a genomic library for complementation of a known mutant of DHDPS; immunological screening of polypeptides expressed from gene libraries; screening a genomic library for hybridization to a radiolabelled oligonucleotide probe, and the like.

The oligonucleotide probe may be synthesized based on sequence derived from genes of other species or from reverse translation of the polypeptide sequence of an isolated DHDPS subunit. Alternatively, the gene may be chemically synthesized wholly or in part.

Once isolated, the gene is characterized using standard recombinant DNA manipulations and molecular analyses. Such techniques are well known to those in the art and are outlined in Maniatis et al., *Molecular cloning: A laboratory manual*, Cold Spring Harbor Laboratory, NY (1982). Typically, the DNA fragment carrying the DHDPS gene is reduced to the smallest functional fragment possible; that is, extraneous DNA flanking the gene is removed by methods such as Ba131 digestion, deletion of a known restriction endonuclease fragment, and the like, to obtain the smallest DNA fragment that will, for example, still complement the DHDPS mutant. This fragment is usually less than three kilobases, more commonly, about one kilobase. The nucleotide sequence of this DNA fragment may then be determined by any of several conventional methods. The open reading frame (coding sequence), the putative RNA polymerase binding site (promoter), ribosomal binding site, and the transcriptional termination signal sequence are then identified. The transcriptional initiation site may be determined by techniques such as S1-nuclease mapping or primer repair analysis. Extracts of bacteria (typically *E. coli*) incorporating the isolated gene on a plasmid are assayed to confirm the presence of DHDPS activity and the in vitro relative resistance of enzymic activity to added L-lysine.

Once characterized, the gene is modified to allow integration, expression, and function of the gene product in host plant cells. The preferred modifications are: 1) the addition of a DNA sequence coding for an amino-terminal chloroplast transit peptide to the 5' terminus of the DHDPS coding sequence; 2) the replacement of bacterial 5' and 3' regulatory sequences with 5' and 3' regulatory sequences recognized by and functional in plant cells; and 3) insertion of this plant-specific expression cassette into a vector suitable for introducing the DHDPS gene into host plant cells, and stably establishing it therein.

Addition of chloroplast transit peptide (CTP) DNA sequence

All lysine biosynthetic enzymes studied in plants to date have been localized in the chloroplasts. Thus, to accomplish proper localization of the product of the foreign gene, a DNA fragment encoding a chloroplast transit peptide sequence is attached to the 5' terminus of the DNA sequence coding for DHDPS, in the proper reading frame, whereby a complete transit peptide-DHDPS preprotein will be translated from transcripts of the gene fusion. Useful transit peptides (typically 40 to 70 amino acids in length) function post-translationally to direct the preprotein to the chloroplast, where the preprotein is imported in an energy-dependent process. The transit peptide is cleaved either during or just after import to yield the mature polypeptide.

The DNA fragment encoding this transit peptide can be obtained from a variety of plant nuclear genes, so long as the products of said genes are expressed as preproteins comprising an amino-terminal transit peptide and transported into chloroplasts. Examples of plant gene products known to include such transit peptide sequences are the small subunit of ribulose bisphosphate carboxylase, ferredoxin, chlorophyll a/b binding protein, chloroplast ribosomal proteins encoded by nuclear genes, certain heat shock proteins, amino acid biosynthetic enzymes such as acetohydroxy acid synthase and 3-enolpyruvylphosphoshikimate synthase, and the like. Alternatively, the DNA fragment coding the transit peptide may be chemically synthesized either wholly or in part from the known sequences of transit peptides, such as those listed hereinabove.

Regardless of the source of the DNA fragment coding the transit peptide, it should include a translation initiation codon and encode an amino acid sequence that is recognized by and will function properly in chloroplasts of the host plant. Attention should also be given to the amino acid sequence at the junction between the transit peptide and the mature DHDPS subunit where the preprotein is cleaved to yield mature DHDPS. Certain conserved amino acid sequences have been identified and may serve as a guideline. Precise fusion of the transit peptide coding sequence with the DHDPS coding sequence may require manipulation of one or both DNA sequences to introduce, for example, a convenient restriction site. This may be accomplished by methods including site-directed mutagenesis, insertion of a chemically-synthesized oligonucleotide linker, and the like.

Function of the chloroplast transit peptide may be assayed in vitro as follows. The transit peptide-DHDPS gene expression cassette may be introduced into any of a number of plasmid vectors, so that the gene is placed in the proper orientation under the transcriptional control of a bacteriophage promoter such as SP6, T3, T7 and the like. The resultant plasmid is then digested at a unique restriction site 3' to the coding sequence to form a linear DNA molecule. This DNA molecule is then subjected to a run-off transcription reaction using an RNA polymerase specific for the promoter being used. Yields of such reactions are typically 10–12 micrograms of essentially pure messenger RNA (mRNA) per microgram of linear DNA template. These mRNA transcripts are then translated in the presence of one or more radiolabelled amino acids using in vitro translation systems such as wheat germ or rabbit reticulocyte lysate, to yield radiolabelled preprotein.

The radiolabelled preprotein is then incubated with isolated intact chloroplasts in the presence of light to assay import efficiency. The chloroplasts are then treated with a protease or combination of proteases such as thermolysin, trypsin, chymotrypsin, and the like. This treatment degrades any protein not sequestered within the chloroplasts. After washing in the presence of protease inhibitors, the chloroplasts are lysed using vortexing, freeze/thaw treatment, reduced osmoticum or a combination of these. The lysate may be: (a) assayed directly, (b) it may be first subjected to immunoprecipitation using DHDPS subunit antibacterial antiserum generated by standard protocols, (c) it may be centrifuged to separate stromal proteins (supernatant) from proteins localized in the thylakoid membranes (pellet), (d) or a combination of these processes may be used. SDS-polyacrylamide gel analysis is used to confirm the presence or absence of a radiolabelled protein band corresponding to the molecular weight of the mature bacterial DHDPS subunit. The presence of the band indicates that the preprotein has been imported and processed to the correct size.

Addition of Plant-Recognized Regulatory Sequences

Expression of the bacterial gene such as DHDPS in plant cells requires regulatory sequences that are recognized by and functional in plant cells. These sequences include a 5' transcriptional initiation region and 3' translational and transcriptional termination regions. The 5' transcriptional initiation region will include the RNA polymerase binding site (promoter). It may also include regions required for regulation of transcription where the regulation is mediated by chemical or physical induction or repression.

Examples of such regulation include light-induced expression of ribulose bisphosphate carboxylase small subunit, heat-induced expression of heat shock proteins, genes regulated by plant hormones or other metabolites, developmentally regulated expression, wound- or stress-induced expression, and the like.

The 5' sequences may also include transcriptional enhancer sequences. The 5' regions may be native to the host plant, or may be derived from other plants where the sequences are functional in the host plant. Suitable sequences may also be obtained from genes of the Ti plasmid of *Agrobacterium tumefaciens*, including octopine synthase, nopaline synthase, mannopine synthase, and the like, or may be obtained from certain viral genes. Alternatively, the transcriptional initiation region may be chemically synthesized either wholly or in part.

The 3' region will include trascriptional termination sequences and may include polyadenylation signal sequences. This region may be derived from the same gene as the 5' sequences or from a different gene. These sequences may also be chemically synthesized.

The resultant expression cassette will comprise a 5' transcriptional initiation region, a chloroplast transit peptide coding sequence, the bacterial DHDPS subunit coding sequence, a translational stop codon, and a 3' transcriptional termination region. The cassette will usually include less than five kilobases, and preferably will include between two and three kilobases.

Insertion of the Expression Cassette in a Vector for Transformation of Plants The choice of a vector for introducing the bacterial DHDPS expression cassette into plant cells will depend on the choice of the transformation method which will, in turn, depend on the host plant and the choice of plant tissue source. A wide variety of protocols are available for the introduction of foreign DNA into the cells of both monocots and dicots, including the use of microprojectiles, microinjection, electroporation, incubation with $Ca^{++}$-precipitated DNA, incubation with liposomes containing the foreign DNA (preferably in the presence of PVA and $Ca^{+2}$), viral systems, and Agrobacterium-mediated transformation. See M. Fromm et al., *PNAS USA*, 82, 5824 (1985) (electroporation), T. M. Klein et al., *Nature*, 327, 70 (1987) (microprojectiles) P. Lurquin et al., *Plant Sci. Lett.*, 25, 133 (1982) (liposomes) and J. Paszkowski et al., *EMBO J.*, 3, 2717 (1984) (use of CaMV gene VI expression signals), the disclosures of which are incorporated by reference herein.

The first five methods are carried out with "naked" DNA where the expression cassette may be simply carried on any *E. coli* cloning vector such as plasmids pBR322, pRK290, pACYC184, and the like. In the case of viral vectors, it is desirable that the system retain replication functions, but lack functions for disease induction.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the foreign gene into the genome of the host plant cell. This vector will also contain sequences that facilitate replication of the plasmid in Agrobacterium cells, as well as in *E. coli* cells.

All DNA manipulations are typically carried out in *E. coli* cells, and the final plasmid bearing the DHDPS expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells.

Regardless of the choice of vector or transformation protocol, identification of transformed plant cells is facilitated by including a gene encoding a function that is selectable in plant cells. Preferred genes are those encoding resistance to a chemical normally inhibitory to plant cells, such as resistance to hygromycin, kanamycin, methotrexate, and certain herbicides. The selectable marker may be carried on a separate plasmid that is co-transformed with the DHDPS-bearing plasmid, or may be carried on the same plasmid as the DHDPS cassette. In the case of Agrobacterium-mediated transformation, the selectable marker can be contained within the region of the plasmid flanked by the T-DNA border regions. Alternatively, a screenable marker such as the β-glucuronidase gene may be used in place of a selectable marker. Cells transformed with this gene may be identified by the production of a blue product on treatment with 5-bromo-4-chloro-3-indoyl-β-D-glucuronide (X-Gluc).

Transformation and Regeneration of Plants

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. Preferably, the tissue source will retain the ability to regenerate whole, fertile plants following transformation.

The transformation is carried out under conditions directed to the plant tissue of choice. The plant cells or tissue are exposed to the DNA carrying the DHDPS expression cassette for an effective period of time. This may range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet, for example) on the surface of solid media plates, separated by a sterile filter paper disk from the plant cells or tissues being transformed.

Following treatment with the DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agent are presumed to be transformed and may be subcultured several additional times on the same medium to remove non-resistant sections. The cells or calli can then be assayed for the presence of the bacterial DHDPS gene cassette, or may be subjected to known plant regeneration protocols. In protocols involving the direct production of shoots, those shoots appearing on the selective media are pressumed to be transformed and may be excised and rooted, either on selective medium suitable for the production of roots, or by simply dipping the excised shoot in a root-inducing compound and directly planting it in vermiculite.

Characterization of Regenerated Plants and Their Progeny

In order to produce transgenic plants exhibiting elevated free lysine levels, the bacterial gene must be taken up into the plant cell and stably integrated within the plant genome. Plant cells and tissues selected for their resistance to an inhibitory agent are presumed to have acquired the gene encoding this resistance during the transformation treatment. Since this marker gene is commonly linked to the bacterial DHDP synthase gene, it can be assumed that the bacterial DHDP synthase gene has similarly been acquired. Southern blot hybridization analysis using a probe specific to the bacterial DHDP synthase gene can then be used to confirm that the foreing gene has been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region.

Once transcribed, the mRNA must be translated by the plant ribosomes into a polypeptide, such as the bacterial DHDP synthase subunit, which must in turn be able to assume a three-dimensional configuration that will confer catalytic activity. Plant cells or tissues shown both to carry and transcribe the bacterial DHDP synthase gene may be further characterized by extraction of the cells or tissues and demonstration of lysine-tolerant DHDP synthase activity. This in vitro lysine tolerance is preferably comparable to that observed in extracts of the microorganism that served as the source of the gene and should be readily distinguishable from the more highly lysine-sensitive native DHDP synthase activity which can be extracted from control plant cells or tissues. Depending on the transcriptional initiation and regulatory sequences used in the construction of the cassette, the activity may be detected in all plant tissues, in selected tissues, or only under selected inducing conditions.

Regardless of the location of the bacterial DHDP synthase activity in the plant, it must be localized within the plant cell so that it can participate in the biosynthesis of lysine, catalyzing the conversion of substrates into product. The ability of the bacterial DHDP synthase to so participate may be assessed by determining the relative tolerance of plant cells or tissues to the lysine analog S-(2-aminoethyl)-cysteine (AEC). Like lysine, AEC is a potent inhibitor of plant DHDP synthase. Plant cells or tissues exposed to inhibitory concentrations of AEC are effectively starved for lysine. DHDP synthase from *E. coli*, however, is considerably less sensitive to this inhibition. The ability of plant cells or tissues expressing active bacterial DHDP synthase to tolerate normally inhibitory concentrations of AEC strongly suggests that the bacterial enzyme is functioning properly in the biosynthesis of lysine.

If the bacterial DHDP synthase is contributing to the biosynthesis of lysine, and if no other mechanisms act to regulate the free lysine pool, free lysine may accumulate to levels higher than seen in control plant cells or tissues. Free amino acid levels may be readily measured by techniques such as reverse phase HPLC analysis of trichloroacetic acid (TCA) extracts of transgenic plant cells or tissues.

Plants that accumulate significantly elevated levels of free lysine in accord with these mechanisms are grown to maturity. These plants are allowed to flower and are self-pollinated or crossed to an appropriate parental line to obtain seed. This seed may then be analyzed for inheritance of the desired trait.

An initial screen of the seed may be germination and seedling growth in the presence of concentrations of AEC that will inhibit the growth of seedlings germinated from control seed. Seedlings demonstrating AEC tolerance may be grown up and fully characterized as described hereinabove for the original regenerate plants.

Plants that may be improved by such a transformation include but are not limited to processed plants (soybeans, canola, potatoes, tomatoes, lupins, sunflower and cottonseed), forage plants (alfalfa, clover and fescue), and the grains (corn, wheat, barley, oats, rice, sorghum, millet and rye). The plants or plant parts may be used directly as feed or food or the lysine may be extracted for use as a feed or food additive.

Although the free lysine levels described herein are elevated in the leaves of transformed plants, it is expected that the present method will allow elevated free lysine levels in other plant organs, including tubers and seeds.

The invention will be further described in accord with the following detailed example.

Example I

A. Materials and Methods

Restriction endonucleases, T4 ligase, polynucleotide kinase, and calf intestine phosphatase were all used according to manufacturer's recommendations. Standard recombinant DNA techniques, transformation of *Escherichia coli* cells, and molecular analyses were performed according to Maniatis et al., *Molecular Cloning: A Laboratory Manual*, Cold Spring Harbor Laboratory, New York (1982).

All in vitro transcriptions (SP6) and translations (rabbit reticulocyte lysate) were done using reagents from Promega Biotec (Madison, WI) and followed the manufacturer's protocols.

Oligonucleotides were chemically synthesized using the phosphoramidite method (Caruthers, *Science*, 230, 281–285 (1985)).

*Agrobacterium tumefaciens* strain LBA4404 (pAL4404) (Hoekema et al., *Nature*, 303, 179–180 (1983)) was used for all plant cell transformations.

The isolation and characterization of the dap A gene has been described in Glassman, "Cloning and Characterization of the dap A Gene of Escherichia coli" (M.S. Thesis, Univ. of Minnesota, Minneapolis, Minn. (1988)), the disclosure of which is incorporated by reference herein.

The gene was isolated from an *Escherichia coli* genomic library (Clarke and Carbon Collection of Hybrid Plasmids, Yale University School of Medicine, New Haven, Conn.). Fragments of a plasmid (pLC1730) reported to carry the dap A gene were subcloned into cloning vector pBR322. Fragments carrying the dap A gene were identified by complementation of a dap A mutant of *E. coli* and confirmed by demonstration of a plasmid-encoded protein of molecular mass 32 kilodaltons (corresponding to the molecular mass of the dihydrodipicolinic acid synthase subunit) and by dihydrodipicolinic acid synthase enzymatic activity. The nucleotide sequence for one such plasmid construct was determined, and putative promoter sequences and a coding sequence for the dap A gene were identified. Extraneous flanking DNA was removed by further subcloning.

Of particular interest are plasmids pDAP1763 and pDAP1205. pDAP1763 carries the entire dap A coding sequence plus 5' and 3' untranslated regions on a 1564 bp NdeI-BstEII fragment. pDAP1205 carries a 1375 bp NdeI-SphI fragment that is missing the last thirteen bases of the coding sequence and all untranslated 3' sequences. Both plasmids are pBR322 derivatives.

B. Chloroplast Transit Peptide Sequence

A DNA sequence encoding a pea chloroplast transit peptide was constructed by first synthesizing subfragments of the sequence and then combining them.

Based on the published sequence for the chloroplast transit peptide of a ribulose bisphosphate carboxylase small subunit gene of pea (Cashmore, in: *Genetic Engineering of Plants*, A. Hollaender, ed., Plenum Press (1983)), eight oligonucleotides (four per strand) were chemically synthesized. The six internal 5' termini bases were phosphorylated using T4 polynucleotide kinase, then 100 pmoles of all eight oligonucleotides were mixed together in a total volume of 70 μl. Ten microliters of this mixture were combined with 100 ng of HindIII-SphI digested pPol26 (Robbins et al., *J. Virol.*, 58, 339-347 (1986)), denatured at 95° C. for 5 minutes, annealed at room temperature for two hours and then ligated to give pSTP31. The synthetic sequence consisted of a HindIII 5' overhang, 30 bp of untranslated leader, 171 bp encoding the 57-amino acid transit peptide (tp), and a 3' SphI overhang which represents the evolutionarily conserved cleavage site for the transit peptide.

C. Modifying the dap A Gene for Use in Plant Cells

Bacterial DNA external to the coding region of the dap A gene was removed and replaced with sequences recognized and processed by plant cells.

In order to add the transit peptide sequence described supra, the 5' terminus of the dap A coding sequence was modified to create an SphI site. This was accomplished by replacing the 108 bp NsiI-NruI fragment in pDAP1763 with a 29 bp synthetic linker which regenerated both the NsiI and the NruI sites. This procedure deleted the bacterial promoter for dap A and changed the sequence surrounding the start codon from CCATGT to GCATGC, thus creating the required SphI restriction site. This change is predicted to result in a phenylalanine-to-leucine substitution at position two in the amino acid sequence. This plasmid was designated pDAP1900.

The 865 bp SphI fragment of pDAP1900 which includes the dap A coding sequence (less the last thirteen base pairs) was ligated into SphI-digested pSTP31 such that the 5'-terminus of the dap A coding sequence was fused to the 3'-terminus of the synthetic transit peptide sequence and the natural cleavage site of the pea small subunit preprotein was restored. The resultant plasmid was designated pDAP4001. The polylinker in this plasmid provided a SacI site just 3' to the end of the coding sequence. This site was used to move the transit peptide (tp)::dap A cassette as a HindIII-SacI 1070 bp fragment into HindIII-SacI cut pGEM3 (Promega Biotec, Madison, Wis.), generating plasmid pDAP4104.

The 3'-terminus of the dap A coding sequence was similarly modified to do four things: (1) destroy the SphI site (rendering the site created at the 5'-terminus unique), (2) restore the last four amino acids of the sequence which had been lost in the original construction of pDAP1205, (3) add two stop codons, and (4) create a BamHI site adjacent to the end of the coding sequence.

This was accomplished by digesting plasmid pDAP1205 with SphI plus BamHI and ligating a 25 bp synthetic linker in place of 147 bp of pBR322 DNA to give plasmid pDAP1252. The destruction of the SphI site resulted in a codon change from alanine to glycine at position 289 in the deduced amino acid sequence.

The newly created BamHI site was used to add transcription termination signals recognized by plant cells. pDAP1252 was digested with BamHI and HindIII and ligated to a 260 bp BamHI-HindIII fragment from pRL101 containing the transcription termination and polyadenylation signal sequences from the nopaline synthase (nos) gene of pTiC58 (nucleotides 673 to 422, Bevan et al. *Nar*, 11, 369-385 (1983)). This construct was designated pDAP1264.

Finally, the modified dap A termini were combined to reconstruct the gene. pDAP1264 was digested with BstEII (in the middle of the dap A coding sequence) and EcoRI (just 3' to the end of the nos poly A sequence) and ligated into BstEII-EcoRI-digested pDAP4104. This plasmid, pDAP4201, carried the synthetic chloroplast transit peptide (STP) sequence fused to the coding sequence of dap A and the nos 3' region, all under the transcriptional control of the SP6 promoter in pGEM3. This construction was used for in vitro analyses of transit peptide function, as described in Section 4, hereinbelow.

For in vivo studies of gene function in plant cells, the STP :: dap A :: nos 3' cassette described hereinabove was placed under the control of the 35S promoter of CaMV as follows. Plasmid p35-227 was derived from pPo126 by inserting the 450 bp BamHI-BglII fragment carrying the 35S promoter sequence from pCaMVPRO (a gift from V. Walbot; see Fromm et al., *PNAS*, 82, 5824-5828 (1985)) into the BamHI site of the pPo126 polylinker. This construction placed a HindIII site just 3' to the promoter. The 1340 bp HindIII fragment of pDAP4201 carrying the entire dap A gene cassette was ligated into this site in the correct orientation to form a functional transcriptional unit for expression in plant cells (plasmid pDAP4307).

D. in vitro Function of Transit Peptide

The ability of the synthetic transit peptide sequence to direct the import and processing of the dap A gene product by intact chloroplasts was assessed using in vitro chloroplast import assays (della-Cioppa et al., *Bio/Technology*, 5, 579-584 (1987)). $^{35}$S-methionine-labelled preprotein for the assay was prepared as follows.

pDAP4201 DNA was digested with EcoRI and subjected to run-off transcription using SP6 polymerase (Melton et al., *NAR*, 12, 7035-7056 (1984)). After removal of plasmid DNA by digestion with RNase-free DNaseI, the mRNA was ethanol-precipitated, resuspended in 25 μl sterile distilled deionized water and quantitated spectrophotometrically. Eight micrograms of this mRNA were used in an in vitro translation reaction (rabbit reticulocyte lysate) which included 2.5 μCi/μl-$^{35}$S-methionine (New England Nuclear, Boston, Mass.) in 145 μl total volume. The reaction mixture was incubated at 30° C. for 90 minutes and stopped by placing it on ice.

Active, intact chloroplasts were isolated from deveined leaves of *Latuca sativa* (romaine lettuce) using a method described for pea seedlings (Bartlett et al., in *Methods in Chloroplast Molecular Biology*, Edelman et al., eds, Elsevier Biomedical Press (1982)). Isolated chloroplasts were resuspended in import buffer (50 mM HEPES, pH 7.6, 0.3M sorbitol), adjusted to 2 mg/ml chlorophyll, and maintained on ice until used.

Fifty microliters of the in vitro translation products (mostly tp:: DHDPS subunit preprotein) were combined on ice with 110 μl import buffer, 25 μl 0.1M L-methionine, 15 μl 0.1M ATP, and 100 μl chloroplasts. The import reaction mixture was placed at an angle and rotated gently directly in front of a 150W fiber optic bulb at room temperature. At 5, 10 and 15 minutes, 70 μl samples were removed and pipetted into eppendorf tubes on ice containing 7 μl of 1 mg/ml thermolysin in 10 mM CaCl$_2$ (Cline et al., *Plant Physiol.*, 75, 675-678, (1984)). A second sample taken at 15 minutes was pipetted into a tube on ice containing 7 μl 10 mM CaCl$_2$ as control. All tubes were incubated on ice for 20 minutes, then diluted with 150 μl import buffer containing 50 mM EDTA to inhibit thermolysin. After centrifuging for 10 seconds, the chloroplasts were resuspended in 50 μl lysis buffer (10 mM HEPES pH 7.5, 10 mM EDTA, 1 mM PMSF, 30 μg/ml aprotinin) and were lysed by two cycles of freeze/thawing and vortexing. The lysates were centrifuged at 14,000×g for 20 minutes to separate the stromal (supernatant) and thylakoid (pellet) fractions.

Stromal protein samples were electrophoresed through a 12.5% SDS-polyacrylamide gel (Laemmli, Nature, 227, 680 (1970)). The gel was stained, dried and subjected to autoradiography. The control sample (no protease) showed a 42 kilodalton band corresponding to the tp : DHDPS subunit preprotein. All three thermolysin-treated samples lacked the 42 kilodalton band and showed instead a band migrating at about 32 kilodaltons that was protected from proteolytic digestion and therefore was concluded to be imported into the chloroplast. The 32 kilodalton protein corresponds to the molecular mass of the mature bacterial dihydrodipicolinic acid synthase subunit.

E. Construction of the Binary Vector pBVI

The following section describes the construction of the vector used for the introduction of the modified dap A into plant cells. The vector comprises the left and right T-DNA borders of pTiAch5 to facilitate integration of the gene into the plant genome, a selectable marker for $E.$ $coli$ (ampicillin resistance), a selectable marker for $Agrobacterium$ $tumefaciens$ and tobacco, (kanamycin resistance), and origin of replication sequences to allow plasmid replication in both $E.$ $coli$ and $Agrobacterium$ $tumefaciens$.

1. Subcloning of the T-DNA borders

The left border of the pTiAch5 $T_L$ DNA was obtained by digesting pOTY8 (Hoekema, supra) with BamHI and ClaI and then isolating a 1206 bp fragment (nucleotides 1 to 1206 according to Barker et al., Plant Mol. Biol., 2, 335–350 (1983); see also DeVos et al., Plasmid, 6, 249–253 (1981)). The fragment was ligated into BglII-ClaI-digested pPo126 to give plasmid pOTBL1.

The right border was similarly obtained from pOTY8 as a 5766 bp HpaI-XhoI fragment inserted into the polylinker region of pPo126 digested with HpaI and XhoI to make pTB11828.

2. Subcloning the pSa origin of replication

The broad host range origin of replication of pSa was isolated by digesting pUCD2 (Close et al., Plasmid, 12, 111–118 (1984)) with HincII and BamHI. The 2900 bp ori fragment was ligated with HpaI-BglII-digested pPo126 to give pPo1Sa.

3. Construction of plasmid containing left and right T-DNA borders and the pSa origin of replication (pBR322LRSa)

The left and right T-DNA borders and the pSa ori were inserted into pBR322 as follows. pOTBL1 was digested with ClaI and HindIII (nucleotide 602, Barker, supra) to generate a 604 bp fragment which was then made bluntended with the Klenow fragment of DNA polymerase. The DNA fragment was inserted into the PvuII site of pBR322 to give pBR322L. The right border was carried on a 912 bp ClaI-BamHI fragment from pTB11828 (nucleotides 13774 to 14686, Barker, supra) and was ligated into ClaI-BamHI-digested pBR322L to make pBR322LR.

The hybrid ClaI site of pBR322LR was sensitive to methylation to $E.$ $coli$ strain MC1000 and therefore refractory to digestion by ClaI. Transferring the plasmid to $E.$ $coli$ strain GM272 (dam−, dcm−)(Marinus et al., J. Bacteriol., 114, 1143–1150 (1973)) allowed the insertion of the 2900 bp EcoRI-ClaI pSa fragment from pPo1Sa into EcoRI-ClaI-digested pBR322LR. The resulting plasmid was designated pBR322LRSa.

4. Construction of a kanamycin resistance marker

A selectable marker capable of conferring kanamycin resistance in both Agrobacterium and in plants was constructed by using the promoter from transcript 24 of the pTiAch5 $T_R$ DNA. This promoter region was isolated as a 1503 bp EcoRI-ClaI fragment from pRK290-EcoΔCla (Gelvin et al., Mol. Gen. Genet., 199, 240–248 (1985)) representing nucleotides 21,631 to 20,128 (Barker, supra). The fragment was ligated into pPo126 digested with EcoRI and ClaI to make pPo1PTR. A BamHI site in the polylinker just 3′ to the transcript 24 promoter was used to insert a 1500 bp BglII-BamHI fragment from Tn5 (Rothstein et al., Cell, 19, 795–805 (1980)). This fragment contains the neomycin phosphotransferase II (NPTII) coding sequence, but lacks the native NPTII promoter. Functional orientation of the fragment with respect to the transcript 24 promoter was confirmed by the ability of the resultant plasmid pPO1NPTII to confer kanamycin resistance on $E.$ $coli$ cells.

Polyadenylation signal sequences from the octopine synthetase (ocs) gene of pTiAch5 were isolated as a 707 bp PvuII fragment from pTB11828 (nucleotides 12,5541 to 11,834, Barker, supra). This fragment was ligated into SmaI-digested pPo1NPTII, replacing 500 bp of extraneous Tn5 sequences 3′ to the NPTII coding sequence. Correct orientation of the poly A fragment was confirmed by the fragment pattern generated by digestion with XmaIII. The plasmid was designated pPo1NPTII-A.

5. Insertion of the selectable marker into pBR322LRSa

The pTR :: NPTII :: ocs 3′ gene cassette was moved as a 3100 bp XhoI fragment from pPo1NPTII-A into SalI-digested pBR322LRSa to make pBV1. This 11.5 kilobase plasmid contained—in a clockwise orientation from the unique EcoRI site—the following components: the broad host range pSa ori, the right border, cloning sites HpaI and BamHI, the pTR/NPTII/ocs chimeric gene (transcribed clockwise), 1415 bp of pBR322 (SalI to PvuII), the left border, and the PvuII-EcoRI fragment of pBR322 which includes the origin of replication and the ampicillin resistance gene.

F. Construction of transformation vector containing the modified dap A gene (pDPZ4474 and pDAP4511)

The unique HpaI and BamHI sites just inside the right border of pBV1 were used to insert the CaMV p35S :: STP31 :: dap A :: nos 3′ cassette. Using sites in the polylinker flanking this cassette in pDAP4307, a 1830 bp SmaI-BglII fragment was ligated into HpaI-BamHI-digested pBV1 to give pDPZ4474. In this construction, the dap A gene is just ahead of the NPTII gene and is transcribed in the same direction as NPTII.

Similarly, a 1830 bp BamHI (partial)-HpaI fragment of pDAP4307 was ligated into HpaI-BamHI-digested pBV1 to give pDAP4511. In this construction, the dap A gene is also just ahead of the NPTII selectable marker, but in the opposite orientation, such that it is transcribed divergently with respect to the NPTII.

pDPZ4474 (ATCC No. 67721) and pDAP4511 were each transformed into $Agrobacterium$ $tumefaciens$ LBA4404 (pAL4404) using the method described in VanVliet et al., Plasmid, 1, 446–455 (1978). Transformants were selected on plates containing kanamycin (50 μg/ml) and streaked out for single colony purity.

G. Transformation of *Nicotiana tabacum* SR1 and regeneration of plants

Cultures of *Agrobacterium tumefaciens* LBA4404 (pAL4404) carrying pDPZ4474, pDAP4511, or pBV1 were used in co-cultivation transformations of tobacco leaf disks. One set of disks was treated with sterile water as a negative control.

Leaf disks of *Nicotiana tabacum* SR1 plants were transformed essentially as described in Horsch et al., *Science*, 227, 1229-1231 (1985) with the following exceptions: Agrobacterium cultures were grown in 523 medium (Kado et al., *Physiol. Plant Pathol.*, 2, 47-59 (1972)), supplemented with rifampicin (20 µg/ml), streptomycin (100 µg/ml), and kanamycin (50 µg/ml) at 28° C. for 48 hours, washed and resuspended in sterile water prior to use with leaf disks; Black Mexican Sweet suspension cultures were used as feeder cultures on nurse plates; all solid media contained 2.5 gm/l Gelrite (Scott Laboratories, Omaha, NE) in place of agar.

After two days on nurse plates, the leaf disks were placed on shooting medium (same as nurse medium, but containing 500 µg/ml carbenicillin and kanamycin at 0, 100 or 200 µg/ml and lacking feeder cultures or filter paper). Plates were sealed with parafilm and incubated at 26° C. with a 12-hour photoperiod. Shoots were excised when they reached 1 cm and were transferred to rooting medium (no hormones) containing carbenicillin and kanamycin at the same concentration on which the shoot originated. When roots appeared, the plantlets were placed in vermiculite and then transplanted to soil.

H. Screening for expression of dap A in regenerated tobacco plants

Plant tissue was initially screened for expression of the introduced dap A gene by evaluating resistance to the lysine analog S(2-aminoethyl)cysteine (AEC). AEC is a potent inhibitor of dihydrodipicolinic acid synthase of plants, but the bacterial DHDPS is much less sensitive to it. Leaf disks were prepared from surface-sterilized leaves as described in the transformation protocol. The disks were placed, (four disks per plate, two plates per treatment) on shooting medium supplemented with 1 mM L-arginine and AEC at 0, 0.1, 0.2 or 0.4 mM. Plates containing shooting medium supplemented with 75 µg/ml kanamycin were included for each plant tested to check the selectable marker. After one week at 26° C. in the light, the individual leaf disks were weighed and the average fresh weight and standard deviation were determined for each treatment.

Leaf disks from all plants remained green and expanded in the absence of AEC. Fresh weight per disk increased from about 9 mg to about 60 mg in 1 week. Growth was strongly inhibited in control plants in the presence of AEC. Leaf disks plated on medium containing at least 0.2 mM AEC were brown and shriveled. In contrast, leaf disks from putative dap A+ plants were readily identified by their ability to remain green and growing in the presence of AEC. Many AEC-tolerant plants were identified using this screening procedure. The characterization of one such plant is described below in detail.

I. Characterization of dap A+ tobacco plant 327

1. AEC tolerance

The response of leaf disks from plant 327 to the presence of AEC was compared with that of leaf disks from water control plant 101. Results are presented in Table 1.

TABLE 1

| | Leaf Disk AEC Screen.* | |
|---|---|---|
| | Fresh Weight (Wt.-% of control) | |
| AEC (mM) | 327 | 101 |
| 0 | 100 | 100 |
| 0.1 | 88 | 32 |
| 0.2 | 81 | 15 |
| 0.4 | 71 | 10 |

*Fresh weights of leaf disks (4 discs per plate, 2 plates per AEC concentration) were measured after one week. Average fresh weights were determined for each AEC treatment and are expressed as the percent of the average fresh weight on plates with no AEC.

2. Lysine-tolerant DHDP synthase activity in leaf extracts

Young leaves of 327 and seed-grown NT-SR1 plants were extracted as follows. One to two grams of deribbed leaves were ground at 4° C. in 2 ml extraction buffer (0.1M potassium phosphate (pH 7.5 at 4° C.), 2 mM EDTA, 1 mM β-mercaptoethanol, 10 mM sodium pyruvate) in the presence of 0.14 gm polyvinylpyrrolidone per gram of tissue. The extract was filtered through Miracloth (Calbiochem) and then centrifuged for 10 minutes at 8000×g (4° C.). The supernatant was slowly brought to 40% saturation by adding finely ground solid ammonium sulfate at 4° C. with gentle stirring. The precipitate was removed by centrifugation. The supernatant was brought to 66% ammonium sulfate saturation and the 40-66% precipitate was collected by centrifugation as before. The pellet was resuspended in column buffer (50 mM Tris-HCl (pH 7.5 at 4° C.), 1 mM EDTA, 10 mM sodium pyruvate, 10% glycerol) and passed through a Sephadex G-25 column (Sigma) to desalt.

Protein concentrations were determined by the dye-binding method of Bradford (REF) using bovine serum albumin fraction V powder in distilled water as the standard.

Dihydrodipicolinic acid synthase activity was monitored using the o-aminobenzaldehyde (ABA) assay (Yugari et al., *J. Biol. Chem.*, 240, 4710-4716 (1965)). L-lysine hydrochloride stock solutions were made in distilled water, filter-sterilized, and added at the indicated concentrations at the beginning of the enzyme reaction. At set time-points, 200 µl aliquots were removed and the reaction quenched in 800 µl of stop buffer (0.21M citric acid, 0.53M sodium phosphate (pH 5 at 25° C.), with 0.24 mg o-ABA added just prior to use from a freshly-made 10 mg/ml absolute ethanol stock). The pink color was allowed to develop for one hour at 25° C. and then the optical density was measured at 520 nm.

DHDP synthase activity in the leaves of 327 was approximately 30-fold higher than that in leaves of seed-grown NT-SR1. More significantly, the enzyme activity in 327 leaves was completely resistant to added L-lysine at 100 µM and only 14% inhibited in the presence of 500 µM L-lysine. In contrast, 100 µM L-lysine inhibited the DHDP synthase activity in NT-SR1 leaves by 87% and no activity could be detected at 500 µM L-lysine.

3. Southern/Northern hybridization analysis

Genomic DNA was isolated from leaves of transformed plants and 101 according to the method of Shure et al., *Cell*, 35, 225-233 (1983). Ten micrograms of DNA from each plant was digested separately with BamHI and with BstEII and electrophoresed through 0.7% agarose. Digestion with BamHI produces a diagnostic 1540 bp internal fragment, whereas BstEII cuts once in the dap A coding sequence. The gel was blotted to a nylon membrane and hybridized (Southern, *J. Mol. Biol.*, 98, 503-517 (1975)), using the 1540 bp BamHI fragment of pDAP4307 labelled with $^{32}$P as a probe. Autoradiography of the blot clearly showed the characteristic 1540 bp band in the BamHI digest track and two bands in the BstEII digest track. These results, coupled with reconstruction markers for copy number, are consistent with the dap A gene being present in transformed plants as a single copy. No hybridization was evident in lanes containing DNA from plant 101.

Northern blot analysis was also performed and the results indicated that the dap A gene was being actively transcribed. Using both total RNA and oligo-dT-selected polyA RNA isolated from the leaves of transformed plants, the same probe described above showed hybridization to a single species of RNA of about 1100 nucleotides. No hybridization to RNA from 101 was observed.

4. Free lysine levels in leaves

Trichloroacetic acid (TCA) extracts of leaves from 327 and 101 were prepared to assay free amino acid levels. Young leaves (1-2 gm) were diced into an ice cold mortar, covered with liquid nitrogen, and ground to a powder. The ground leaves were lyophilized overnight and dry weights determined. Each lyophilized sample was returned to a cold mortar and reground in the presence of 2 ml 10% TCA. The mortar was rinsed with an additional 2 ml of TCA. The TCA extracts were combined and incubated on ice for 30 minutes with occasional vortexing. The extraction mixture was centrifuged for 20 minutes (4° C.) and the supernatant was removed and placed on ice. The pellet was re-extracted with 2 ml 10% TCA as before and the supernatants were pooled. Two milliliters of the pooled extract were extracted three times with 5 ml ether. The ether extract was stored at −70° C. until analyzed.

Free amino acid levels were determined by reverse phase HPLC using the o-phthaldialdehyde derivatization method of Jones et al., *J. Chromatog.*, 266, 471-482 (1983). Three samples of NT-SR1 leaves averaged 75 µg free lysine per gram lyophilized tissue. Two samples of 327 leaves gave values of 15,450 and 14,630 µg free lysine per gram lyophilized tissue, respectively, or about a 200-fold increase in free lysine.

5. Heritability of the dap A gene

Tobacco plant 327 flowered and was allowed to self-pollinate and produce seed. Mature, dry seed was collected, surface-sterilized with 10% bleach, and rinsed well with sterile water. Seeds were plated (50 seeds per plate, two plates per treatment) on gridded germination plates (¼ MS salts, 2.5 gm/l Gelrite) containing AEC at 0, 1, 10, 30, 100 and 300 µM AEC. Seeds from self-pollinated 101 were treated identically as controls. All seeds germinated in 3-4 days. After 10 days, the number of green seedlings on each plate was counted. After two weeks, the seedlings were gently pulled from the Gelrite and root lengths were measured. Results are shown in Table 2 and clearly demonstrate that the AEC tolerance trait is inherited by the progeny of 327.

TABLE 2

| | AEC Resistance in Seedlings. | |
|---|---|---|
| | Avg. Root Length (% of control) | |
| AEC (µM) | 327 | 101 |
| 0 | 100 | 100 |
| 1 | 111 | 46 |
| 3 | 87 | 33 |
| 10 | 51 | 27 |
| 30 | 46 | 18 |

TABLE 2-continued

| | AEC Resistance in Seedlings. | |
|---|---|---|
| | Avg. Root Length (% of control) | |
| AEC (µM) | 327 | 101 |
| 100 | 21 | 0 |

Root lengths measured at two weeks post-plating. Average root lengths were determined for each AEC treatment and results are expressed as percent of average root length on medium lacking AEC.

The invention has been described with reference to various specific and preferred embodiments and techniques. However, it should be understood that many variations and modifications may be made while remaining within the spirit and scope of the invention.

What is claimed is:

1. A method of increasing the level of free L-lysine in a plant comprising:
   (a) introducing a foreign gene into the cells of a dicotyledonous plant tissue source; and
   (b) expressing said foreign gene in said cells, wherein a first DNA sequence of said gene encodes dihydrodipicolinic acid synthase (DHDPS) which is substantially resistant to feedback inhibition by endogenously-produced free L-lysine, and wherein said foreign gene further comprises a second DNA sequence attached to the 5'-terminus of the first DNA sequence which encodes a chloroplast transit peptide (CTP) which localizes the DHDPS in the chloroplasts of said cells.

2. The method of claim 1 wherein said DHDPS gene is a bacterial gene.

3. The method of claim 1 wherein said CTP DNA sequence is substantially identical to a CTP DNA sequence obtained from a plant nuclear gene encoding a preprotein comprising an amino-terminal CTP.

4. The method of claim 1 wherein a plasmid comprising said foreign gene is introduced into the cells.

5. The method of claim 4 wherein said plasmid is a bacterial cloning vector.

6. The method of claim 5 wherein said plasmid is an *E. coli* cloning vector.

7. The method of claim 1 wherein the foreign gene is introduced into said plant cells by the techniques of electroporation, microinjection, microprojectiles, or liposomal encapsulation.

8. The method of claim 4 wherein the foreign gene is introduced into the plant cells by Agrobacterium-mediated transformation.

9. A transformed plant cell containing a foreign gene which expresses a chloroplast transit peptide (CTP), and which expresses dihydrodipicolinic acid synthase (DHDPS) which is substantially resistant to feedback inhibition by endogenously-produced free L-lysine.

10. The plant cells of claim 9 wherein said DHDPS gene is a bacterial gene.

11. The plant cell of claim 10 wherein said DHDPS gene is an *E. coli* dap A gene.

12. The plant cell of claim 10 wherein said CTP is a pea CTP.

13. A transformed dicotyledonous plant which produces free L-lysine by a biosynthetic pathway employing dihydrodipicolinic acid synthase, (DHDPS), wherein said DHDPS is the product (a) of a foreign gene which also expresses a chloroplast transit peptide, and (b) is substantially resistant to feedback inhibition by endogenously-produced free L-lysine.

14. The transformed plant of claim 13 wherein said foreign DHDPS gene is a bacterial gene.

15. The transformed plant of claim 14 wherein said foreign gene is an *E. coli* dap A gene.

16. The transformed plant of claim 13 comprising levels of free L-lysine which are at least about 50 times higher than the levels in an untransformed plant of the same species.

* * * * *

UNITED STATES PATENT AND TRADEMARK OFFICE
CERTIFICATE OF CORRECTION

PATENT NO. : 5,258,300
DATED : November 2, 1993
INVENTOR(S) : Kimberly F. Glassman et al.

It is certified that error appears in the above-indentified patent and that said Letters Patent is hereby corrected as shown below:

Column 2 Line 58 "race" should read -- rice--therefor.

Column 3 Line 54 "exogeneous" should read --exogenous--therefor.

Column 3 Line 55 "endogeneously" should read --endogenously--therefor.

Column 5 Line 60 "semialdchyde" should read --semialdehyde-- therefor.

Column 5 Line 61 " dihydropicoline" should read --dihydrodipicoline-- therefor.

Signed and Sealed this

Thirteenth Day of August, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,258,300

DATED : November 2, 1993

INVENTOR(S) : Linda J. Barnes et al.

It is certified that error appears in the above-identified patent and that said Letters Patent is hereby corrected as shown below:

In column 20, line 49, please delete "cells" and insert --cell-- therefor.

In column 20, line 53, please delete "10" and insert --9-- therefor.

Signed and Sealed this

Twenty-fourth Day of August, 1999

*Attest:*

Q. TODD DICKINSON

*Attesting Officer*  *Acting Commissioner of Patents and Trademarks*